(12) United States Patent
Matusch

(10) Patent No.: US 8,597,233 B2
(45) Date of Patent: Dec. 3, 2013

(54) CYLINDER-PISTON UNIT SUITABLE FOR STORING INJECTION SOLUTIONS FOR A NEEDLE-FREE AUTOMATIC OR MANUAL FILLING OF THE CYLINDER-PISTON UNIT, ALSO UNDER ATMOSPHERIC PRESSURE

(75) Inventor: Rudolf Matusch, Marburg (DE)

(73) Assignee: LTS Lohmann Therapie—Systeme AG, Andernach (DE)

(*) Notice: Subject to any disclaimer, the term of this patent is extended or adjusted under 35 U.S.C. 154(b) by 27 days.

(21) Appl. No.: 13/304,469

(22) Filed: Nov. 25, 2011

(65) Prior Publication Data

US 2012/0101431 A1    Apr. 26, 2012

Related U.S. Application Data

(63) Continuation-in-part of application No. PCT/EP2010/002975, filed on May 14, 2010.

(30) Foreign Application Priority Data

May 29, 2009 (DE) .......................... 10 2009 023 334

(51) Int. Cl.
   *A61M 5/30* (2006.01)
(52) U.S. Cl.
   USPC ............................................ 604/68; 604/218
(58) Field of Classification Search
   USPC ................. 604/68–72, 122, 218, 219, 187
   See application file for complete search history.

(56) References Cited

U.S. PATENT DOCUMENTS

| 2,567,673 A * | 9/1951 | Lawshe ........................... 604/68 |
| 5,312,335 A | 5/1994 | Kckinnon et al. |
| 5,626,567 A | 5/1997 | Gmeiner |
| 2005/0240159 A1 | 10/2005 | Kito et al. |
| 2008/0146997 A1 | 6/2008 | Hoffmann |
| 2008/0287885 A1 | 11/2008 | Hoffmann et al. |
| 2009/0159553 A1 | 6/2009 | Hoffmann et al. |
| 2009/0166978 A1 | 7/2009 | Hoffmann et al. |
| 2009/0254036 A1 | 10/2009 | Asmussen et al. |
| 2009/0281496 A1 | 11/2009 | Matusch |

FOREIGN PATENT DOCUMENTS

| EP | 0 511 183 A1 | 10/1992 |
| EP | 1 557 190 A1 | 7/2005 |
| EP | 1 875 934 A1 | 1/2008 |
| FR | 2 613 628 A1 | 4/1987 |
| WO | WO 2006/128915 A1 | 12/2006 |

* cited by examiner

*Primary Examiner* — Theodore Stigell
(74) *Attorney, Agent, or Firm* — R.S. Lombard; K. Bach (57) ABSTRACT

A pressure-stable cylinder/piston unit which blocks water vapor and oxygen and is designed for a needle-free injector, with a chamber arranged in a cylinder, which blocks water vapor and oxygen, and designed for long-term and sterile storage of an injection solution, an end wall with at least one nozzle bore or one outlet element, a pressure-stable outer cylinder, and a pressure-stable piston arranged movably in the chamber and blocking water vapor and oxygen. Methods for bubble-free, automatic or manual filling of the cylinder/piston unit, also at atmospheric pressure are also disclosed.

7 Claims, 9 Drawing Sheets

CYLINDER-PISTON UNIT SUITABLE FOR STORING INJECTION SOLUTIONS FOR A NEEDLE-FREE AUTOMATIC OR MANUAL FILLING OF THE CYLINDER-PISTON UNIT, ALSO UNDER ATMOSPHERIC PRESSURE

CROSS-REFERENCE TO RELATED APPLICATION

This is a continuation-in-part application of pending international application PCT/EP2010/002975 filed May 14, 2010 and claiming the priority of German Application No. 10 2009 023 334.2 filed May 29, 2009.

BACKGROUND OF THE INVENTION

The invention relates to a pressure-stable cylinder/piston unit which blocks water vapor and oxygen and is designed for a needle-free injector, with a chamber arranged in a cylinder, which blocks water vapor and oxygen, and designed for long-term and sterile storage of an injection solution, an end wall with at least one nozzle bore or one outlet element, a pressure-stable outer cylinder, and a pressure-stable piston arranged movably in the chamber and blocking water vapor and oxygen.

The invention further relates to methods for bubble-free, automatic or manual filling of the cylinder/piston unit, also at atmospheric pressure.

Cylinder/piston units are used in injectors and disposable injectors which are known, for example, from US 200810146997 A1 DE 10 2007 004 211 A1 or DE 10 2007 008 369 A1. None of these cylinder/piston units is suitable for long-term storage of injection solutions, e.g. over a year, since they are unable to block water vapor and oxygen.

Injection solution is understood as liquid medicaments. The specialist terms used will now be explained in detail. The term medicament is known to the person skilled in the art. This is understood as substances or mixtures of substances for human or veterinary medicine. They consist of the pharmaceutical active substance or substances, and of further standard components that make this active substance usable pharmaceutically, in particular water.

DE 10 2005 054 600 A1 discloses a cylinder/piston unit having a cylinder and a piston which is guided therein, wherein the cylinder and the piston enclose a chamber that can be filled at least for a time with an active substance, and the cylinder has at least one outlet element at its front end. The cross section of the chamber or the cross section of the cylinder inner wall increases at least in regions from the front to the back. At least in the front area directed toward the outlet element, the piston has a front elastic skirt, the front outer edge of which defines, when the piston is unloaded, a cross-sectional surface which is greater than a surface that is defined by a contour line and that lies in the area of transition from the skirt to the section of the piston carrying the skirt.

DE 10 2006 040 888 B3 discloses a closure system for containers used for storing or administering substances in the form of liquids, pastes or powders, said system consisting of a cap, provided with a through-hole, and of a closure element. The cap holds the closure element with a force fit and/or form fit on the container by means of a catch element present on the container in the area of the opening that is to be closed. The end face which surrounds the opening of the container, and on which the closure element bears, has a depression. The closure element is a virus-proof, bacteria-proof and spore-proof film that lies on the end face and, at least in some areas, over the depression. When the cap is fitted in place, an elastomer ring or adhesive ring is arranged between the closure element and the depression and fills the depression.

DE 10 2006 045 959 B3 discloses a cylinder/piston unit including a cylinder and a piston guided in the cylinder and sealed off in a sterile manner by a rubber seal, wherein the cylinder and the piston enclose a chamber that can be filled at least for a time with active substance, and the cylinder has at least one outlet element at its front end. The piston, resting in a rear position, is sealed off relative to the cylinder in a sterile manner by a static rear sealing element, wherein both sealing elements each respectively bear on the wall of the cylinder and on the wall of the piston in a sealing position. Arranged spatially behind each static sealing element, there is a parking area for receiving the respective sealing element. When the piston is actuated, the individual static sealing elements are transferred from their respective sealing position to a parked position located in the parking area, wherein each sealing element in the parked position touches either only the cylinder wall or only the piston wall. Arranged between the two static sealing elements, there is at least one dynamic sealing element on the piston side, which dynamic sealing element bears on the inner wall of the cylinder at least when the piston is actuated.

In the described cylinder/piston unit, a closure element is inserted as a piston into the prefilled medicament chamber in the vacuum application process. Under vacuum, the closure element is placed on the liquid level of the medicament that has been introduced into the chamber. This method and the devices required for it are expensive and complicated.

Proceeding from this prior art, the objects of the invention are object 1—to define a pressure-stable cylinder/piston unit which blocks water vapor and oxygen and is designed for long-term sterile storage of an injection solution, and methods for bubble-free filling of the cylinder/piston unit, also in a tray, where the piston can be introduced more easily and at atmospheric pressure into the cylinder, in order to reduce the costs for the device and the method. At the same time, however, it is also intended to allow manual filling, for example of small batch numbers, such that, for example, no filling machine is needed for the clinical specimens;

object 2—to safely avoid underdosing (partial administration) or no dosing (rebound of the injection stream) (no wet-shot);

object 3—to avoid the return flow of injection solution from the injection channel;

object 4—to avoid the bubble formation that is possible starting from administration volumes of more than 150 microliters.

SUMMARY OF THE INVENTION

These objects are achieved in the first instance by the device of claim 1. Accordingly, the pressure-stable cylinder/piston unit which blocks water vapor and oxygen is characterized in that the chamber is designed with a first chamber and a second, concentric chamber, wherein the cross section of the first chamber is greater than the cross section of the second chamber, and each nozzle bore or each outlet element is closed in a sterile manner by a membrane that blocks water vapor and oxygen and that opens at an overpressure. By means of such a configuration, a contact surface or annular surface is created on which the piston comes to bear, e.g. with a U-profile seal that is squeezed upon insertion into the first chamber and allows air to escape.

Object 2 is achieved by the design of the nozzle outlet.

The nozzle outlet ends in a raised (protruding) truncated cone, such that the skin is pressed on during injection, and the injection solution penetrates the skin at relatively low pressure. This is helped by the underlying subcutaneous fatty tissue, which constitutes looser tissue compared to the cutis. Since the stream of injection solution does not impact the skin in free flight, it also cannot partially or completely rebound off the surface. It is quantitatively administered, and a wet-shot is avoided.

Object 3 is achieved by plug-like closure of the skin. Since the nozzle outlet is closed by the piston, in particular the inner piston body, the raised truncated cone forms a plug at the injection site. If it is left in place for a few seconds on the skin until the pressure in the skin has dropped as a result of the distribution of the injection solution, no return flow can occur.

Object 4 is achieved by a multi-nozzle model, e.g. a four-nozzle model, such that up to 0.6 milliliter can be administered free of bubble. Experience shows that needle-free subcutaneous injections with volumes of greater than 150 microliters cause subcutaneous bubble formation. The version presented here by way of example has four outlet elements and is therefore able to administer injection volumes of up to 0.6 milliliter, By a preferred embodiment of the piston in an inner piston body with flange and an outer piston ring that blocks water vapor and oxygen and provides a sterile seal, for example in the form of a U-profile or of a sterile seal with another shape that overlaps the flange blocking water vapor and oxygen, different materials may be considered for the piston. For closing the chamber, or the second chamber filled with injection solution, and for the subsequent possible storage for up to one year, the outer piston ring is made of a rubber approved for medicine, e.g. West 4590. Upon insertion into the first chamber, the outer piston ring is pressed such that a channel or a flow edge arises through which the displaced air can escape from the chamber without pressure. A gas cushion, located entirely in the second chamber, remains between the piston and the injection solution. In a further step, this gas cushion is removed from the second chamber by means of the chamber being inverted (air to nozzle) and the inner piston body of the piston being pressed into the second chamber. The flange and the external diameter of the inner piston body are adapted to the internal diameter of the second chamber. When air is removed completely from the second chamber, the inner piston body is located entirely within the second chamber. The guiding of the inner piston body is at all times ensured by a configuration of this kind.

During the subsequent injection of the injection solution by means of a drive unit, the cylinder/piston unit is received by, for example, spring hooks of the drive unit. An alternative embodiment involves screwing the cylinder/piston unit into the drive unit, providing it with a flange or bayonet closure.

For the injection, the engaged closure cap with the membrane fitted over it is removed, and, with the aid of the piston rod actuated by the drive unit (for example by a pretensioned spring), the inner piston body with flange is pushed in as far as the end of the second chamber and so quickly that the speed of the stream of liquid emerging from the nozzle(s) is sufficient for penetration of the skin.

In a preferred embodiment, the inner piston body is designed with at least one sealing lip, wherein the leaktightness between the inner piston body and the wall of the second chamber increases as the pressure rises.

The abovementioned object is also achieved by a method using the cylinder/piston unit just described above. The method comprises at least the following steps:

filling a second chamber with an injection solution, wherein the volume of the injection solution is smaller than the volume of the second chamber;

inserting a piston, designed for example with a squeezed U-profile ring seal, into a first chamber until it bears on an annular surface in order to close the second chamber, wherein a gas cushion remains in the second chamber;

rotating the piston/cylinder unit through ca. 180° about the horizontal axis and waiting until the gas cushion in the second chamber has risen fully upward to at least one nozzle bore or one outlet element;

moving an inner piston body with flange, by means of a piston rod, out of the outer U-profile piston ring into the second chamber, wherein the gas cushion is forced through the nozzle bore(s) or outlet element(s) from the second chamber, and, upon emergence of the gas cushion, a closure cap with membrane, or a separate membrane acting as overpressure valve, lifts away from the nozzle bore(s) or outlet element(s) and annular pressure contours A, B and C, and, after the emergence of the gas cushion, again closes the nozzle bore(s) or outlet element(s) on the annular pressure contours A, B and C in a sterile manner (overpressure valve function), The method ensures that the cylinder/piston unit is completely filled and that, without further measures, it can be separately stored or can be used in a drive unit. Providing the closure cap with a membrane ensures at all times that the injection solution remains sealed in a sterile manner at three places on the annular pressure contours A, B and C.

For manual filling, e.g. for clinical tests, the piston is positioned about 2-3 mm in front of the annular surface. With the nozzle pointing upward, the injection solution is injected through the outer piston ring into the chamber. By advancing the piston as far as the annular surface, and by further advancing the inner piston body with flange, the air is forced through the overpressure valve formed by the membrane.

In a development of the method, it is proposed that the complete emergence of the gas cushion is detected. For this purpose, for example, the nozzle bore(s) or outlet element(s) is/are monitored by a light barrier for the emergence of the injection liquid. As soon as a change is detected, the insertion of the inner piston body is directly stopped.

Since the air requires a much lower advancing force of the piston than does the injection solution, the switching-off of the piston advance can also be thereby controlled.

With the present-day accuracy of liquid metering and the precision of injection-molded chambers, it is also possible to compute the advance movement of the piston rod. In the case of small batch numbers, the movement of the air bubble is monitored by sight.

BRIEF DESCRIPTION OF THE DRAWINGS

Further features and details of the invention will become clear from an illustrative embodiment depicted in schematic drawings, in which.

In all of the figures, the same technical elements are designated by the same reference signs.

DETAILED DESCRIPTION OF THE PARTICULAR EMBODIMENTS

Figure 1:
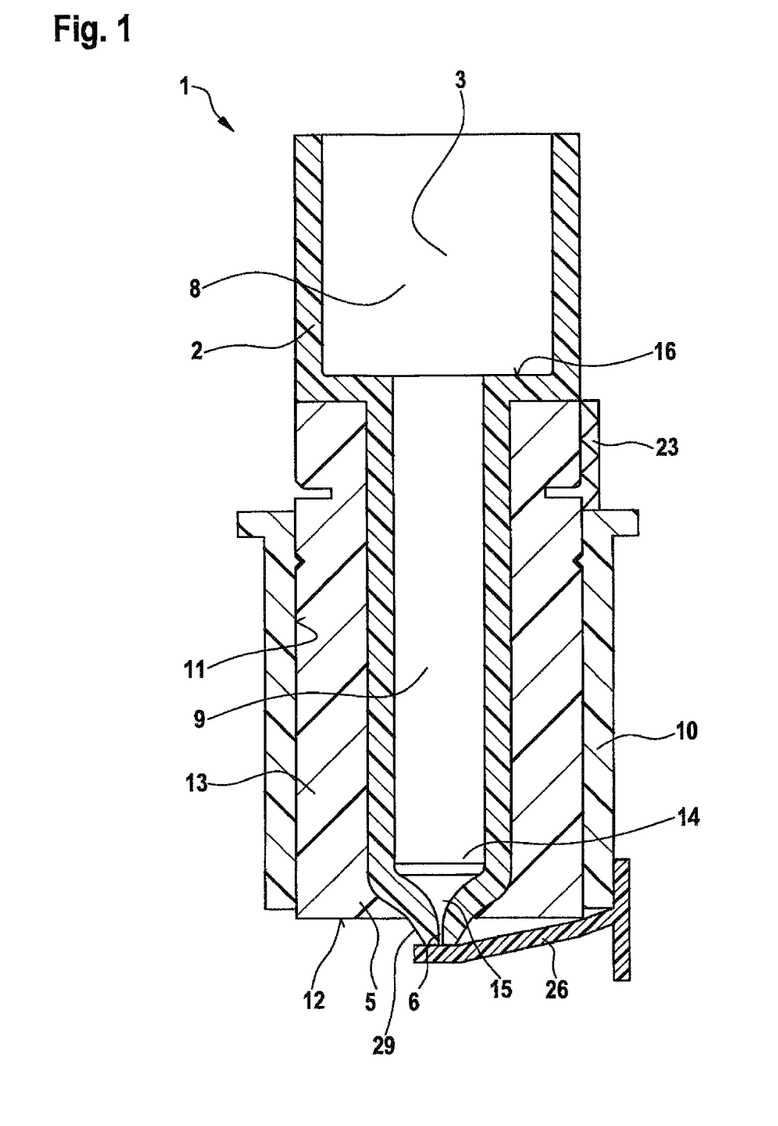
FIG. 1 shows a sectional side view of a cylinder of a cylinder/piston unit, with an engaged closure cap with membrane.

FIG. 1 is a sectional side view of a cylinder/piston unit 1. A chamber 3 of a cylinder 2 that blocks water vapor and oxygen is formed by a first chamber 8 and by a second, concentric chamber 9, wherein the cross section of the first chamber 8 is greater than the cross section of the second chamber 9. A pressure-stable outer cylinder 13 substantially surrounds in contacting relationship the cylinder 2 proximate the second chamber 9. On the side directed away from the first chamber 8, proximate the second chamber 9 the outer cylinder 13 on the outside 12 thereof includes an end wall 5, which has at least one nozzle bore or at least one outlet element 6 passing therethrough. Each nozzle bore or each outlet element 6 ends on the outside 12 of the pressure-stable outer cylinder 13 in a raised truncated cone 29 proximate end wall 5 and has, on an inside 14 of the chamber 9, an outflow funnel 15. On the outside 12 of the pressure-stable outer cylinder 13, a membrane 26, for example made of rubber or transparent silicone, that blocks water vapor and oxygen, is stretched over the outlet element(s) 6 and preferably supported by the closure cap 10. Alternatively, a membrane 27 can be secured on the outer cylinder 13 as a sterile closure and overpressure valve.

Between the first chamber 8 and the second chamber 9, a transition area is formed, preferably as an interior annular surface 16 of cylinder 2. A first embodiment of the transition area provides radii (not shown) at the transition from the cylindrical wall of the first chamber 8 to the annular surface 16 and from the annular surface 16 to the cylindrical wall of the second chamber 9. A second embodiment of this area provides bevels (not shown). Other embodiments, including combinations of, for example, radii and bevels, negative or positive camber, and concave or convex, can be considered. The embodiments help, on the one hand, when filling the injection solution 4 (see FIG. 2) and, on the other hand, when producing the cylinder 2, which is produced for example by an injection molding technique or from glass. By virtue of the embodiments described, above, the flow behavior of the particular material blocking water vapor and oxygen is supported, in order to achieve a cylinder 2 with the predetermined properties such as perpendicularity, concentricity, wall thickness, etc.

Figure 2:
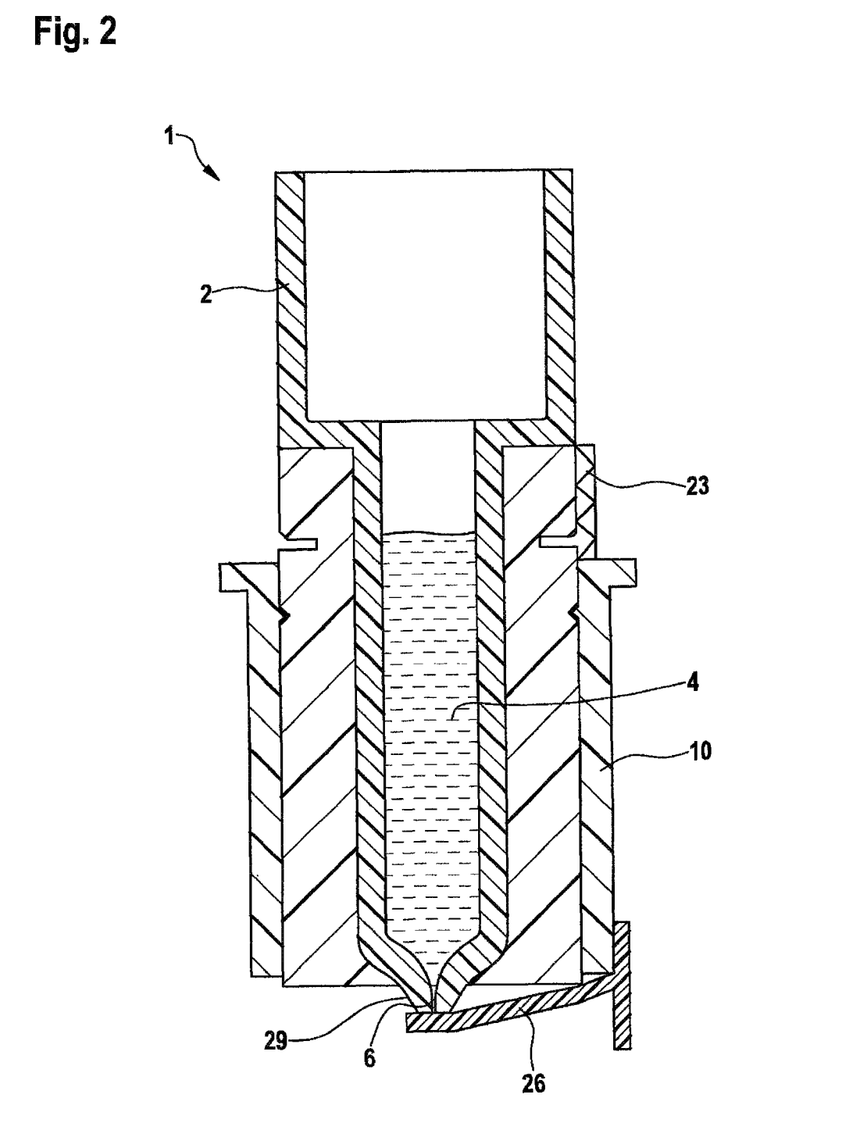
FIG. 2 shows the cylinder from FIG. 1 sitting, for example, in the tray in the filling machine, after sterile filling of the injection liquid only into the second chamber.

Using known devices, the injection solution 4 is introduced into the second chamber 9 in such a way that the second chamber 9 is not completely filled. The filling is carried out under atmospheric pressure. The filling of each cylinder 2 is carried out separately or in groups, wherein, for example, twenty cylinders in a matrix of four×five in a tray are filled simultaneously.

Figure 3:
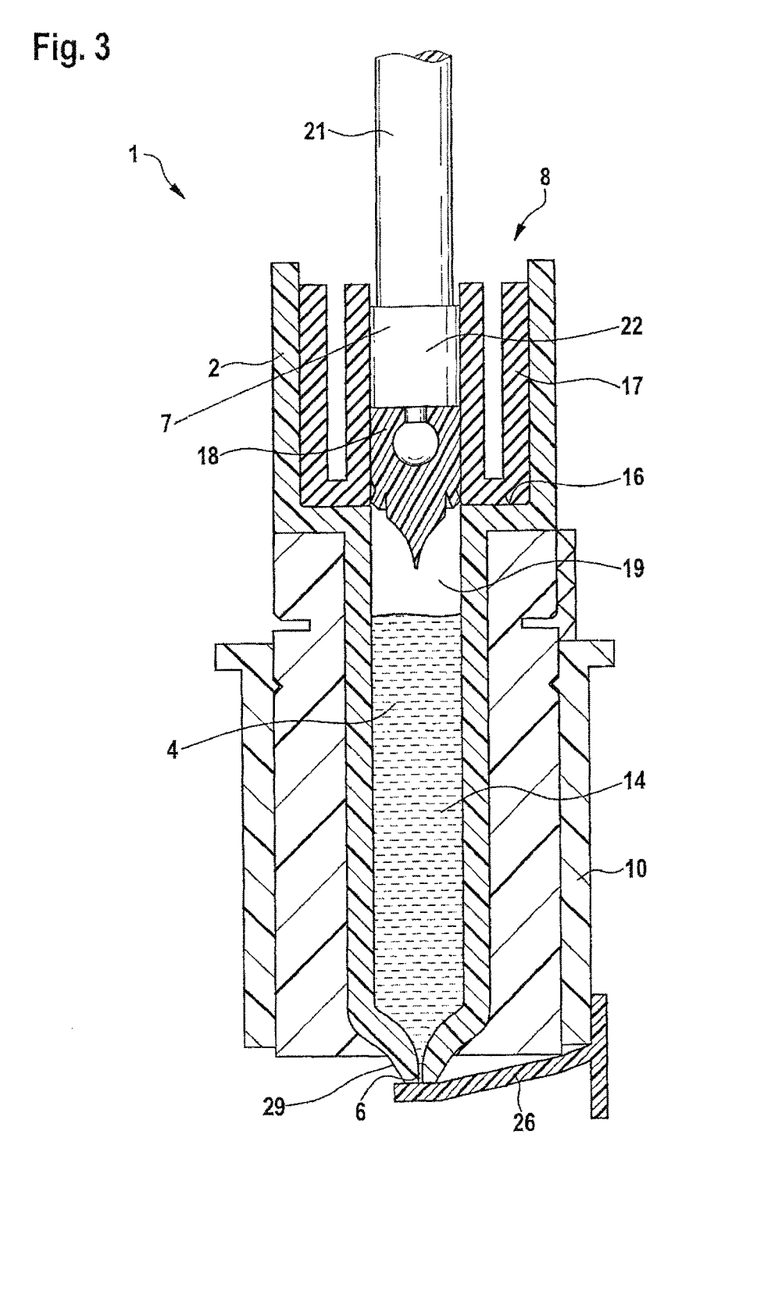
FIG. 3 shows the cylinder from FIG. 2 after the piston, consisting of an inner piston body with flange and of an outer piston ring, has been inserted in a pressure-free, sterile manner into the first chamber, flush onto the annular surface not wet with injection solution, and a remaining air pocket.

A piston 7 as a multi-part closure element is then pushed into the first chamber 8 at atmospheric pressure, as is shown in FIG. 3. The closure element, composed of an outer piston ring 17 and of an inner piston body 18 with a flange 22 that blocks water vapor and oxygen, is pushed into the first chamber 8 until contact is made with the annular surface 16. The outer piston ring 17 is squeezed laterally by the setting head of the filling machine, such that when it is inserted into the first chamber 8 it does not exert any pressure on the injection solution 4 located in the second chamber 9. Methods and devices for pressure-free insertion of a stopper or of a closure piece are known. For example, the outer piston ring 17 is deformed such that the gas, in the present case air, located between closure element and injection solution 4, is not compressed and instead can escape. After removal of the setting head, the U-profile sealing ring closes in a sterile manner, blocking water vapor and oxygen.

Figure 4:
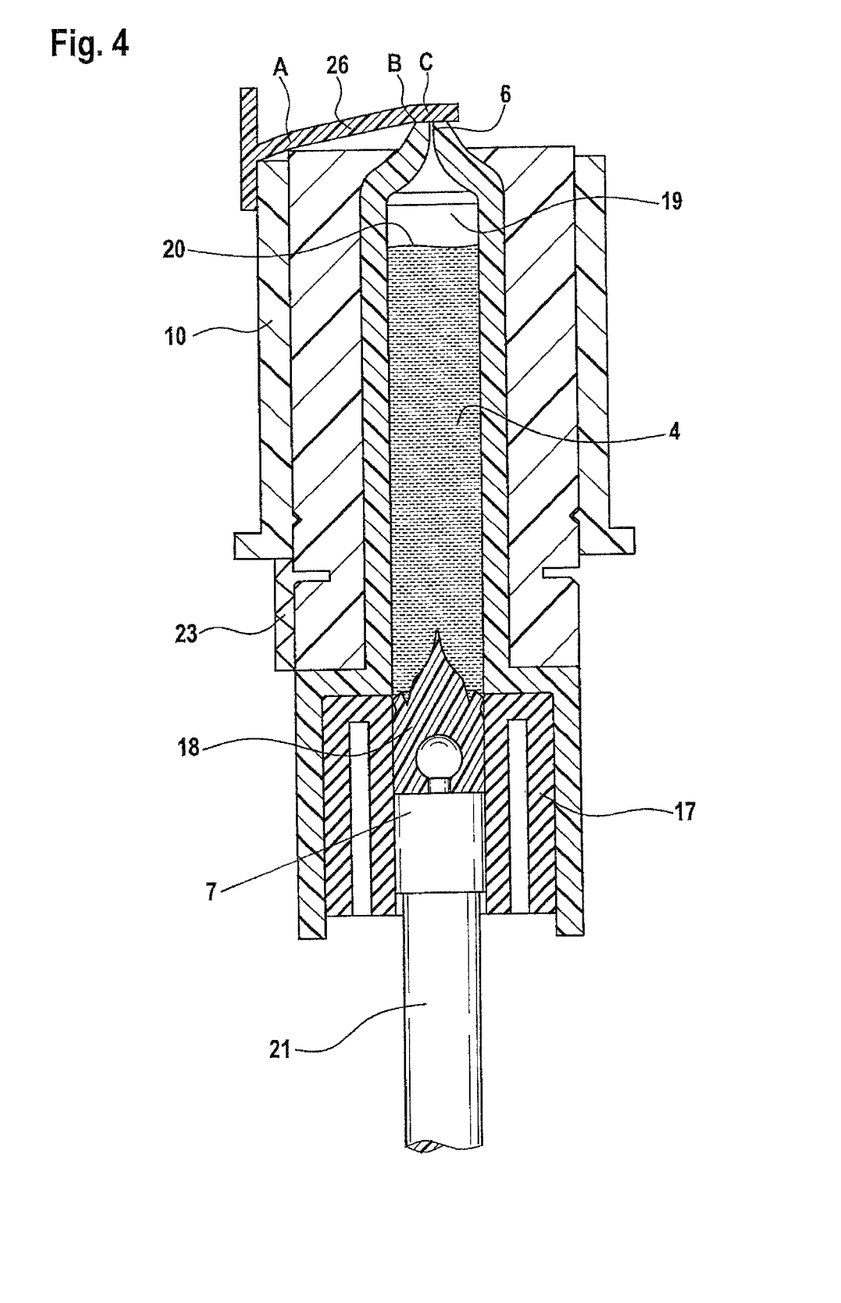
FIG. 4 shows a sectional side view of the cylinder/piston unit rotated through 180 about the horizontal axis, such that the air pocket migrates to the outlet nozzle.
Figure 5:
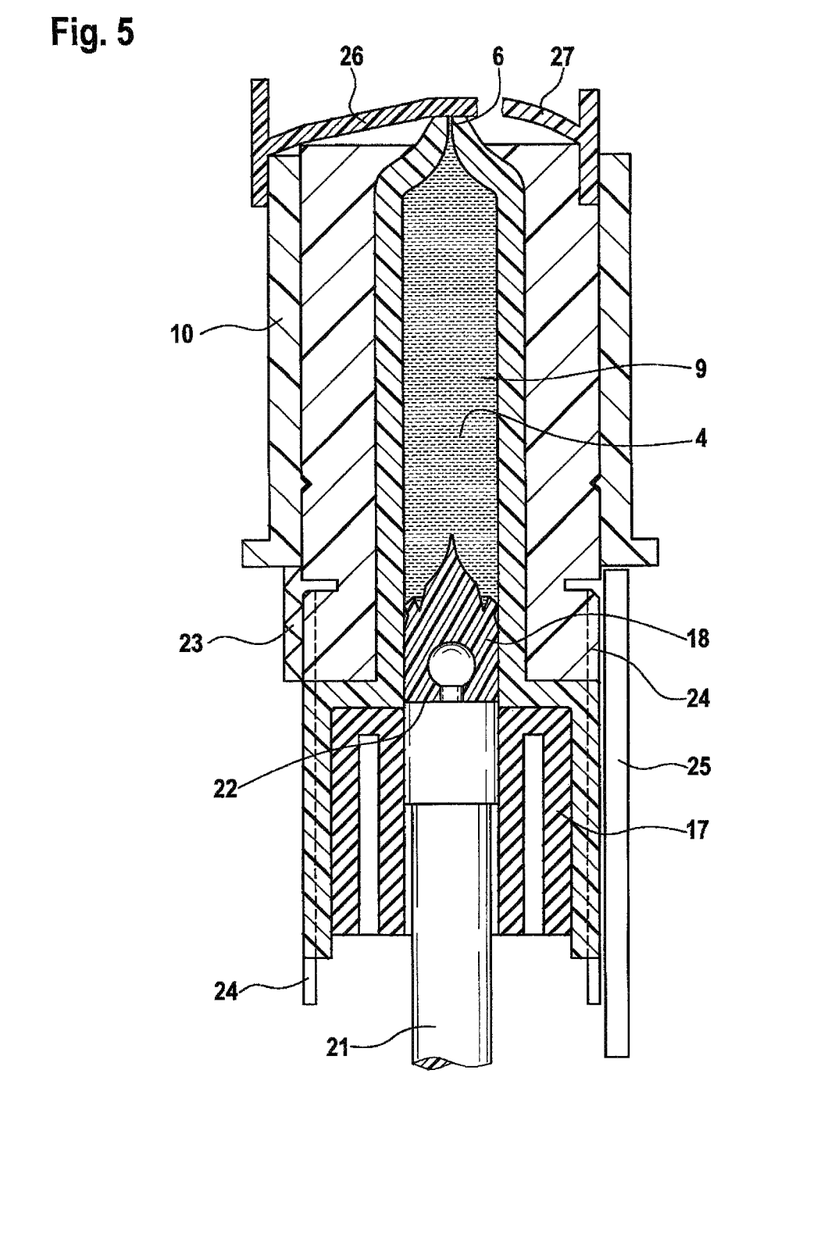
FIG. 5 shows a sectional side view of the cylinder/piston unit according to FIG. 4, wherein the injection solution completely fills the second chamber; additionally alternative membrane fitting, spring hook and trigger.

After placement of the piston 7, composed of the outer piston ring 17 and of the inner piston body 18 with flange 22, which can also be designed separately from a piston rod 21, a gas bubble/air pocket 19 and the injection solution 4 are located in the second chamber 9. To remove the gas bubble/air pocket 19, the cylinder/piston unit 1 is rotated through ca. 180° about the horizontal axis. The end wall 5, with the attached closure cap 10 and the membrane 26, now points upward, as is shown in FIG. 4. The gas bubble/air pocket 19 located in the second chamber 9 rises to the top and is located between the upper edge 20 of the injection solution 4 and the nozzle bore(s) or outlet opening(s) 6. When the gas bubble 19 is entirely located over the upper edge 20 of the injection solution 4 (the time needed for this depends on, among other things, the viscosity of the injection solution 4, the surrounding temperature etc., and is taken into consideration in the subsequent method steps), the inner piston body 18 of the closure element is moved upward by means of the piston rod 21 and the flange 22. The outer piston ring 17 remains fixed in position, bearing on the annular surface 16. The inner piston body 18 with flange 22 is pushed into the second chamber 9 until the gas bubble/air pocket 19 has escaped completely through the nozzle bore(s) or outlet opening(s) 6 from the second chamber 9, as is shown in FIG. 5. For this purpose, a membrane 26 of the closure cap 10 lifts away from the annular pressure contours A, B and C when there is an overpressure in the second chamber 9. The sterile air thus passes the sterile membrane 26 and escapes through the gap between the cylinder and the transparent closure cap 10. The complete expulsion of the gas bubble/air pocket 19 from the second chamber 9 is detected by measurement methods and measurement devices known per se (light barrier), by means of the injection solution 4 being detected in the nozzle bore(s) or outlet opening(s) 6. Another variant involves the inner piston body 18 being pushed into the second chamber 9 as far as a predetermined position. In a further variant, the advance movement is switched off under electronic control when the advancing force of the piston abruptly increases after the air escapes.

As is shown in FIG. 5, the piston rod 21 is designed with a flange 22, although the flange 22 can also be designed separately from the piston rod 21. In the case of a fully filled chamber 9, the edge of the outer piston ring 17 is flush with the flange 22 of the piston rod 21. The diameter of the pretensioned sealing lip 31 of the inner piston body 18 is chosen such that, with rising pressure, it can engage sealingly in the second chamber 9 upon ejection of the injection solution 4 from said second chamber 9. The pressure-stable outer cylinder 13 is designed, on the jacket surface 11, with retainer elements 23, such as a slit, thread, flange or bayonet. The drive unit of the disposable injector is designed to complement the shape of the retainer elements 23. In order to eject the injection solution, the inner piston body 18 with flange 22 is moved by the piston rod 21 in the direction of the end wall 5. This is done, for example, by a pretensioned spring, as is described in more detail in the abovementioned documents concerning disposable injectors. Cylinder 2 and flange 22 must block water vapor and oxygen during a twelve-month period of storage of the cylinder/piston unit filled with injection solution 4.

Besides glass, suitable materials for the cylinder 2 and the flange 22 are also transparent, amorphous thermoplastics, e.g. a copolymer based on cycloolefins and ethylenes or α-olefins (COC or COP).

The outer cylinder 13 has to be able to withstand for a short time (a few milliseconds) a pressure of up to 350 bar and must therefore be made of a pressure-stable material, for example polycarbonate (PC) or polyurethane (PU).

The material used for the inner piston body 18 is a tetrafluoroethylene/hexafluoropropylene copolymer (FEP). This has self-lubricating properties in conjunction with the aforementioned materials of the cylinder 2 or inner part, such that no separate lubricants are needed between the inner piston body 18 and the cylinder 2. Alternative materials that can be chosen include perfluoroalkoxy copolymer (PFA), tetrafluoroethylene (E TFE) or polyvinylidene fluoride (PVDF).

The material used for the outer piston ring 17 is a rubber, such as Helveot FM 257, Heivoet FM 460, Stelmi 6422, Stelmi 6720 or West 4590. The membrane 26 can be made of the same materials that close in a sterile manner and block water vapor and oxygen.

Figure 6:
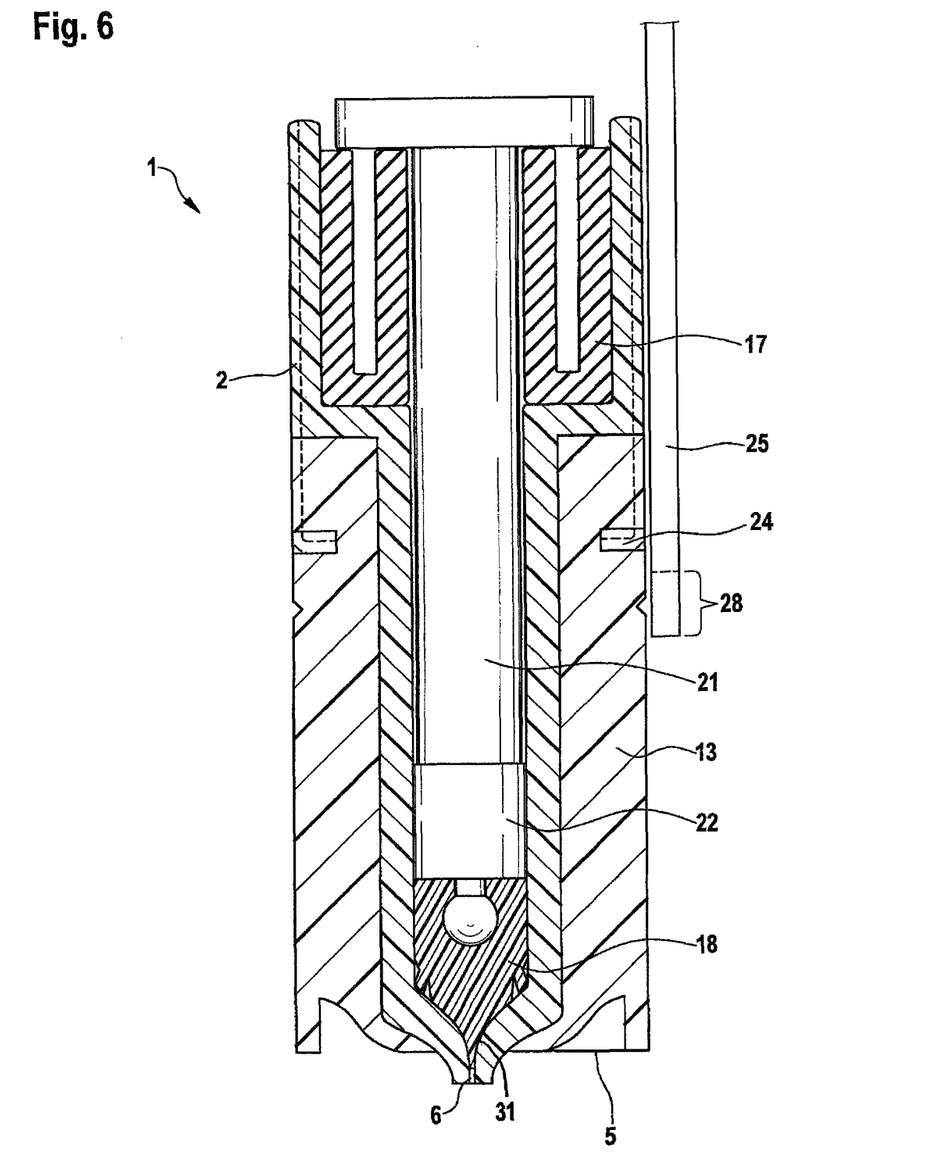
FIG. 6 shows a cylinder/piston unit after removal of the closure cap with membrane and actuated injection; trigger path.

FIG. 6 shows a cylinder/piston unit 1 after removal of the closure cap with membrane 26 and actuated injection. An alternative configuration of the outside of the end wall 12 is shown on the left-hand side. By virtue of the raised configuration of the cone 29 surrounding the nozzle 6, the skin is pressed on and therefore more easily traversed by the injection stream. The injection solution 4 then spreads out in the subcutaneous fatty tissue, which is looser compared to the cutis. Quantitative administration is ensured in this way. Since the nozzle 6 is closed by the inner piston body 18 lying at the bottom, the truncated cone 29 acts as a lid on the skin channel, such that a return flow of the injection solution is avoided. After a few seconds, the pressurized in section solution has become distributed in the looser subcutaneous fatty tissue, and the injection channel in the skin has contracted. The injector can then be removed from the injection site.

Figure 7:
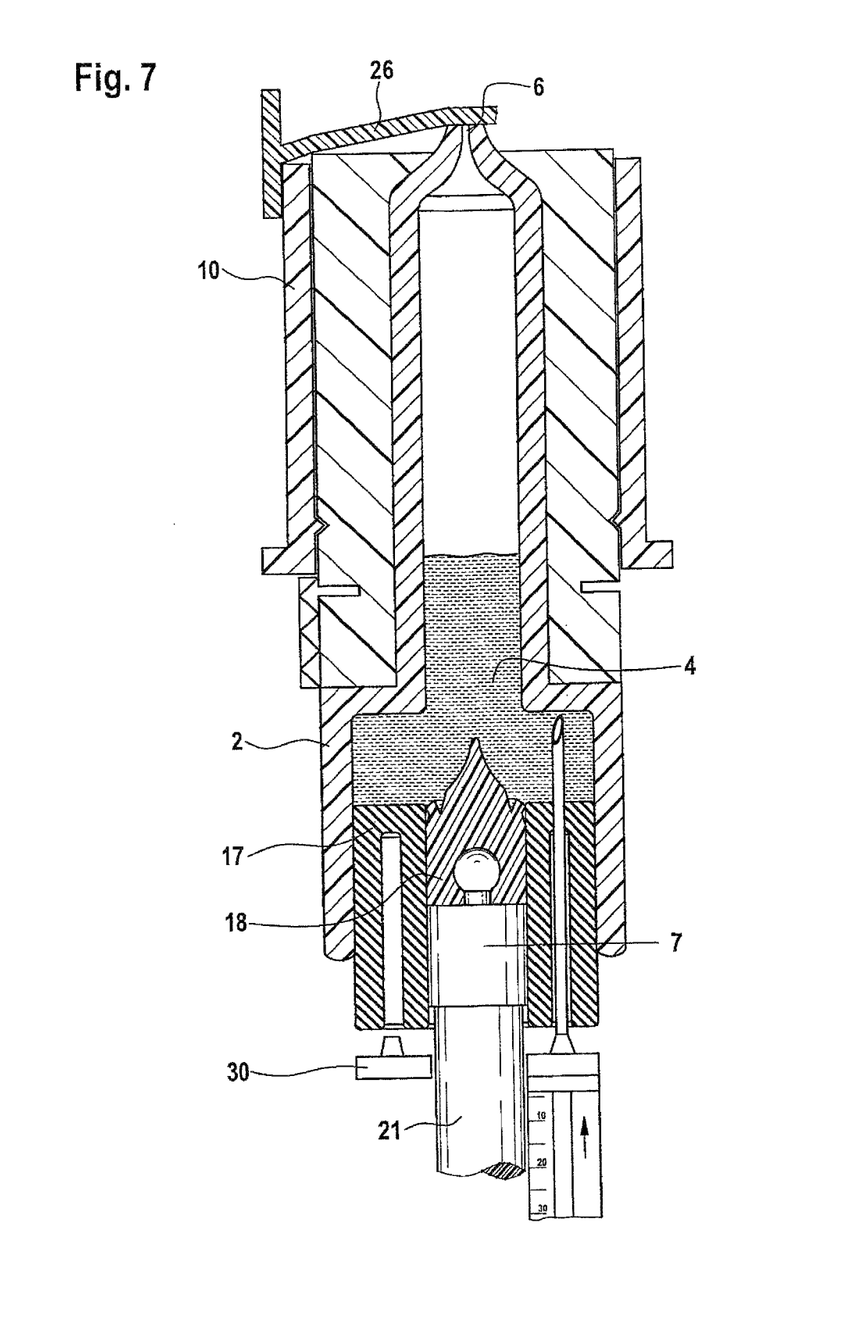
FIG. 7 shows manual filling of the single-nozzle cylinder/piston unit using a syringe.

FIG. 7 shows sterile filling by hand, e.g. for a clinical test, without a complicated filling machine. For this purpose, at the time of manufacture, the piston unit 7, consisting of inner piston body 18 with flange 22 and of outer U-profile piston ring 17 closed by a profile ring 30, is placed into the first chamber 8 only 2-3 mm in front of the annular surface 16. This cylinder/piston unit 1 is then gamma-sterilized. The sterile profile ring 30 can then be removed in the hospital. The needle of a syringe filled with injection solution can then be inserted into the hollow space of the U-profile 17, the U-profile rubber 17 pierced, and the rest of the first chamber 8 and part of the second chamber 9 filled, with the nozzle 6 in the upper position. After the injection needle has been removed, the piston unit 7, consisting of inner piston body 18 with flange 22 and outer U-profile piston ring 17, is advanced as far as the annular surface 16, such that the air 19 remaining in front of the nozzle 6 is then displaced as in FIG. 5. After it has been connected to the drive unit, the system is then ready for storage or administration.

Figure 8:
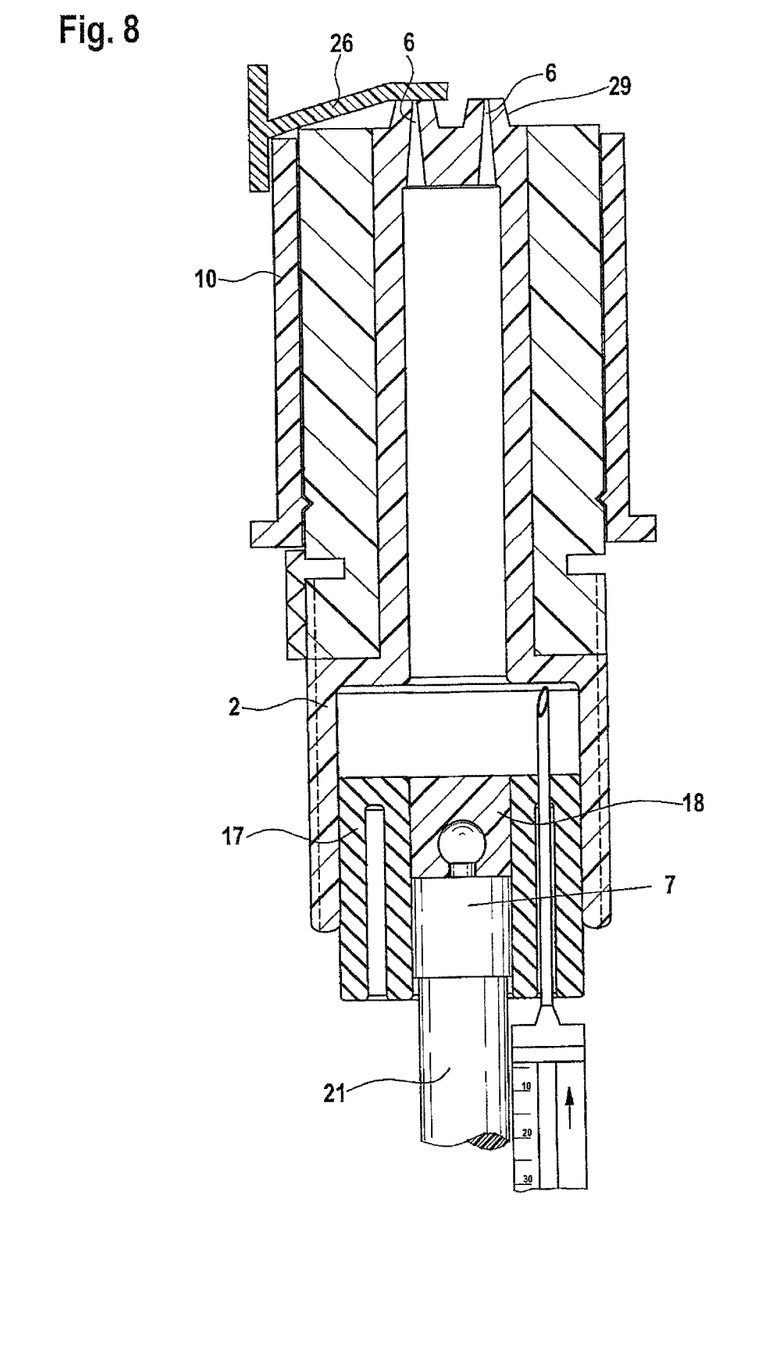
FIG. 8 shows manual filling of the multi-nozzle cylinder/piston unit using a syringe.

In the same way as is shown in FIG. 7, a multi-nozzle cylinder/piston unit can be filled by hand, as shown in FIG. 8. The mechanical filling is done analogously to the single-nozzle version.

Figure 9:
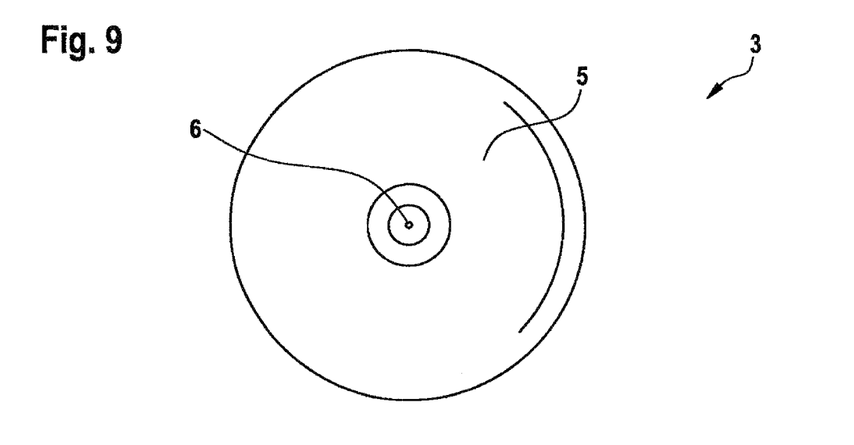
FIG. 9 shows a bottom view of the end wall of a cylinder with one nozzle.

FIG. 9 shows a bottom view of a version of the cylinder 3 with an end wall 5 and one nozzle 6.

Figure 10:
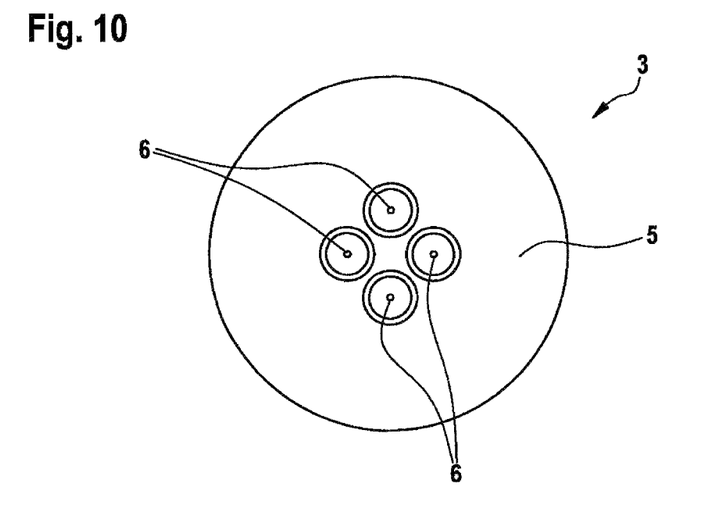
FIG. 10 shows a bottom view of the end wall of a cylinder with four nozzles.

FIG. 10 shows a bottom view of a version of the cylinder 3 with an end wall 5 and four nozzles 6.

LIST OF REFERENCE SIGNS 1 cylinder/piston unit
2 cylinder, blocking water vapor and oxygen
3 chamber
4 injection solution
5 end wall
6 nozzle bore or outlet element
7 piston, consisting of outer piston ring 17, inner piston body 18 and flange 22
8 first chamber
9 second chamber
10 closure piece
11 jacket surface
12 outside end wall
13 outer cylinder, pressure-stable
14 inside of chamber or of outflow funnel
15 outflow funnel
16 annular surface
17 outer piston ring, U-profile ring
18 inner piston body
19 gas bubble/air pocket
20 upper edge
21 piston rod
22 flange of the piston rod, also separate design
23 retainer element
24 spring hook
25 trigger, trigger tube
26 membrane on closure piece 10
27 membrane on cylinder, alternatively
28 trigger path
29 cone, truncated
30 profile ring
31 sealing lip of inner piston body 18
A, B, C annular pressure contours

What is claimed is:

1. A pressure-stable cylinder/piston unit (1) which blocks water vapor and oxygen and formed for a needle-free injector, the pressure-stable cylinder/piston unit (1) characterized by:
a chamber (3) arranged in a cylinder (2), the chamber (3) for long-term and sterile storage of an injection solution (4),
a pressure-stable outer cylinder (13) having a jacket surface (11), the pressure-stable outer cylinder (13) including an end wall (5) with at least one nozzle bore or one outlet element (6) passing therethrough,
a pressure-stable piston (7) arranged movably in the chamber (3) and blocking water vapor and oxygen,
the chamber (3) formed with a first chamber (8) and a second, concentric chamber (9), wherein the cross section of the first chamber (8) is greater than the cross section of the second chamber (9), the pressure-stable outer cylinder (13) substantially surrounds the cylinder (2) in contacting relationship proximate the second chamber (9), a transition area between the first chamber (8) and the second chamber (9) is formed as an interior annular surface (16) of cylinder (2)

and each nozzle bore or each outlet element (6) is closed in a sterile manner by a membrane (26, 27) for blocking water vapor and oxygen and the membrane (26, 27) opens at an overpressure, and the piston (7) comprising an inner piston body (18) and a flange (22), and an outer compressible piston ring (17) having an inner through hole approximating the outer diameter of the flange (22) and the inner piston body (18) and second concentric chamber (9), the inner piston body (18) and flange (22) in slideable pass-through relationship with respect to the outer compressible piston ring (17), the inner piston body (18) and the flange (22) when positioned in the first chamber (8) are axially surrounded in gas sealing relationship by the outer compressible piston ring (17) for blocking water vapors and oxygen in a pressure stable and sterile closing manner during long term storage of the injection solution (4) within the second concentric chamber (9), the inner piston body (18) and the flange (22) in slideable contacting relationship with cylinder (2) proximate the second concentric chamber (9) in preparation for and during injection, the outer compressible ring (17) together with the inner piston body (18) and the flange (22) during long term storage of the injection solution (4) substantially occupying the entire first chamber (8) in gas sealing relationship therewith, the outer compressible piston ring (17) at the distal end thereof in direct contacting and gas sealing relationship with the interior annular surface (16) of the cylinder (2) during long term storage of the injection solution (4).

2. The cylinder/piston unit as claimed in claim 1, further characterized by the membrane (26) is connected to a closure piece (10), or the membrane (27) is formed separately removable and forms a sterile closure piece and overpressure valve.

3. The cylinder/piston unit as claimed in claim 2, further characterized by the closure piece (10) is formed releasably connected directly or indirectly to the jacket surface (11) or to the outside (12) of the end wall (5) of the cylinder (13) or to a trigger tube (25).

4. The cylinder/piston unit as claimed in claim 1, further characterized by the outer piston ring (17) being laterally deformable.

5. The cylinder/piston unit as claimed in claim 4, wherein the outer piston ring (17) has a U-profile.

6. The cylinder/piston unit as claimed in claim 1, further characterized by the inner piston body (18) and the flange (22) of the piston rod (21) are formed, along with the outer piston ring (17), and the latter along with the cylinder (2), to provide a sterile seal blocking water vapor and oxygen.

7. The cylinder/piston unit as claimed in claim 1, further characterized by the inner piston body (18), at the edge directed toward the second chamber (9), is provided with at least one sealing lip (31) that seals more tightly as the pressure increases.

* * * * *